United States Patent [19]

Plugge

[11] 4,047,522
[45] Sept. 13, 1977

[54] HYDROTHERAPEUTIC APPARATUS

[76] Inventor: Jerome R. Plugge, Rte. 50,, Skipton, Cordova, Md. 21625

[21] Appl. No.: 705,252

[22] Filed: July 14, 1976

[51] Int. Cl.² .................... A61H 9/00; A61H 33/00
[52] U.S. Cl. ..................................... 128/66; 128/370
[58] Field of Search ................ 128/65, 66, 24.1, 399, 128/400, 370; 4/178, 180, 182

[56] References Cited
U.S. PATENT DOCUMENTS

| | | | |
|---|---|---|---|
| 3,027,568 | 4/1962 | Blau et al. | 128/370 X |
| 3,234,935 | 2/1966 | Bell et al. | 128/66 |
| 3,272,201 | 9/1966 | Burns | 128/66 |
| 3,571,818 | 3/1971 | Jacuzzi | 4/180 |

Primary Examiner—Lawrence W. Trapp
Attorney, Agent, or Firm—Brady, O'Boyle & Gates

[57] ABSTRACT

A unitized and easily transportable therapeutic bath assembly for the limbs of a race horse or other animals, including humans, consisting of a fiber-glass tub body having a cubical tank adapted to receive one or more of the animal's limbs, for example, the legs. An evaporator unit is located in a recess of a tank wall adjacent an enclosed compartment housing a refrigeration unit and circulating pump which is respectively coupled to the evaporator unit and tank. Also, an air compressor located in the enclosed compartment is coupled to the tank for providing agitation of a cooled liquid circulated through the tank.

15 Claims, 7 Drawing Figures

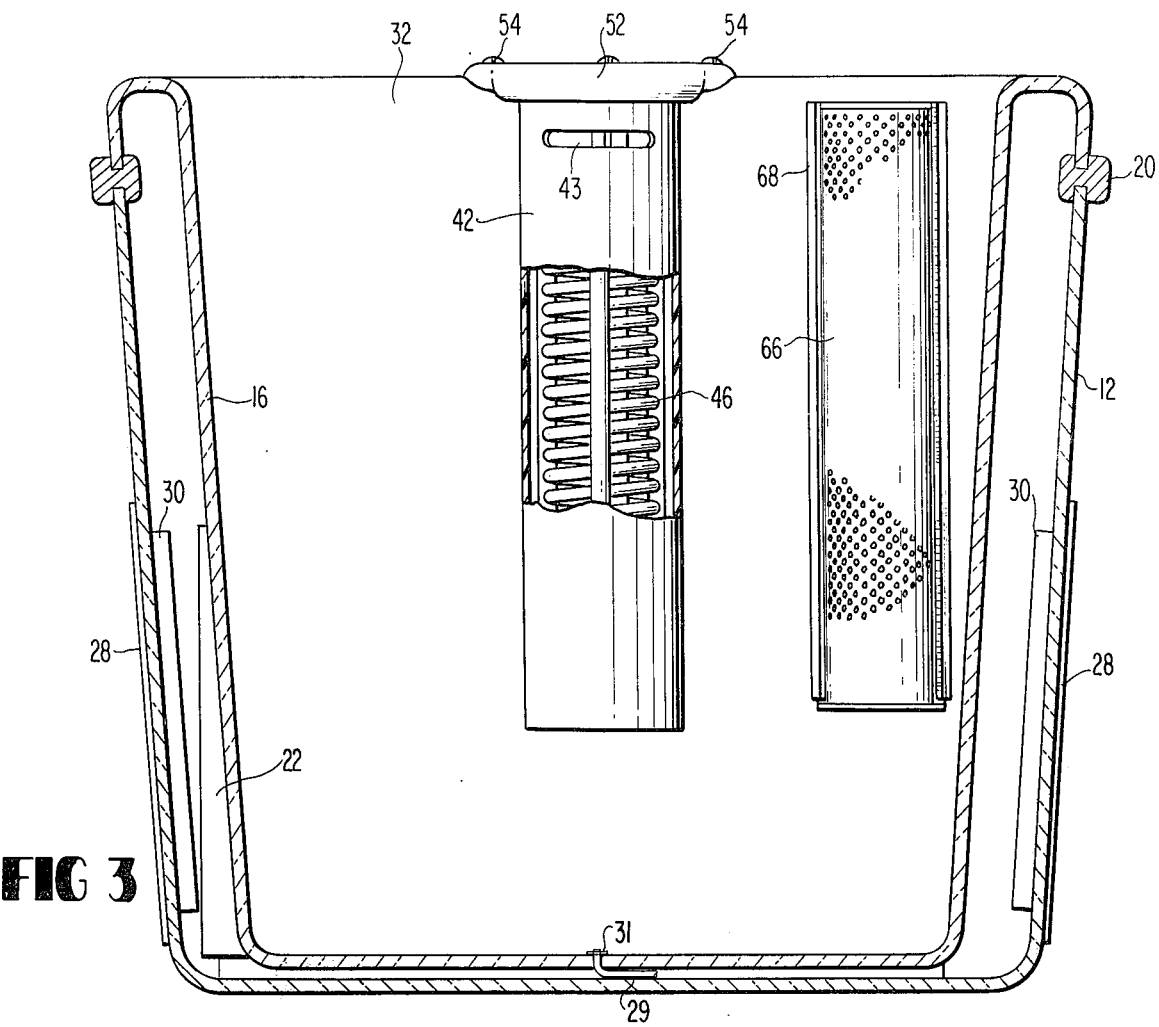
FIG 3
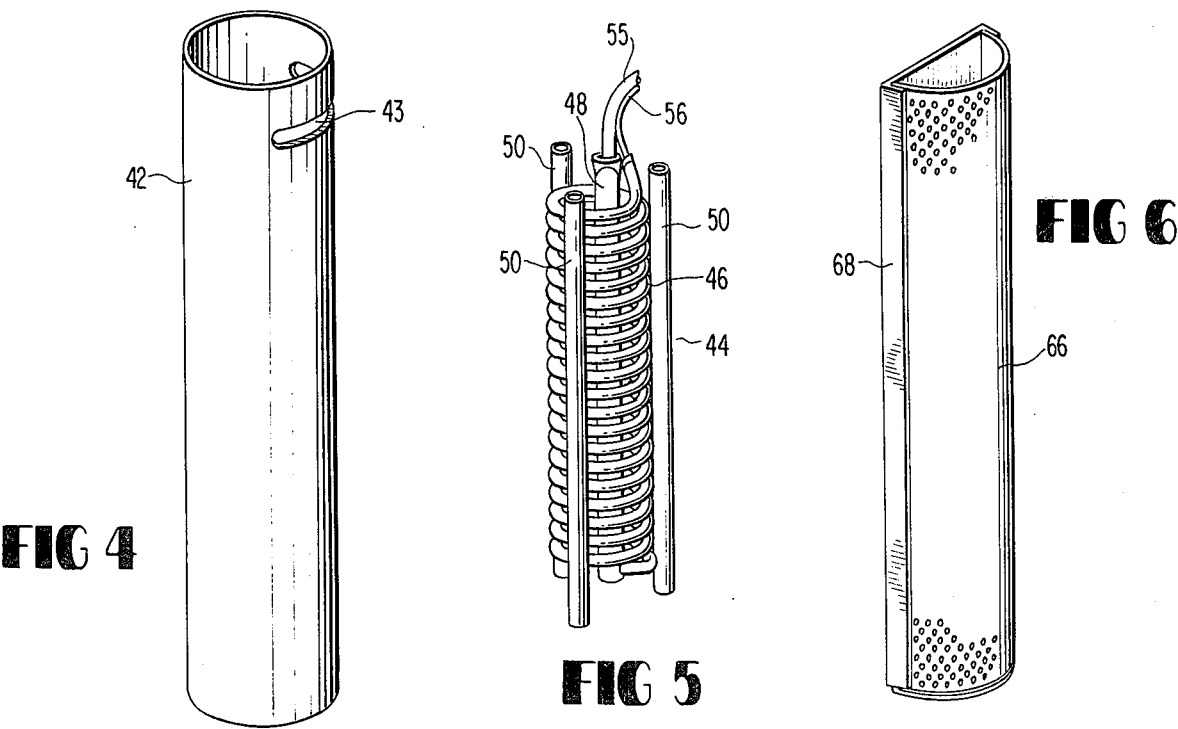
FIG 4
FIG 5
FIG 6

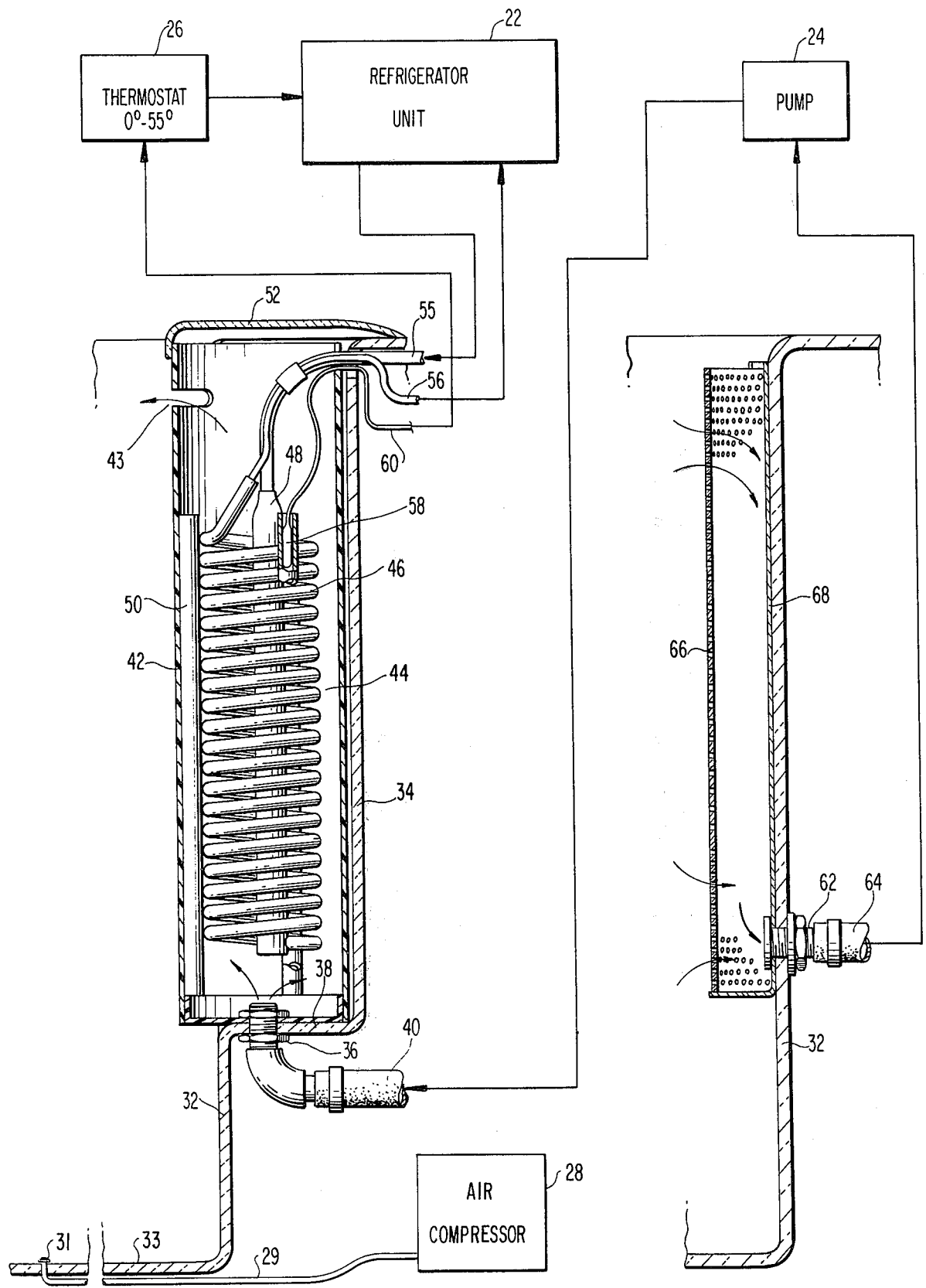

HYDROTHERAPEUTIC APPARATUS

BACKGROUND OF THE INVENTION

This invention relates generally to therapeutic apparatus and more particularly to hydrotherapeutic apparatus for the treatment of the limbs of animals, including humans.

Animals and particularly race horses are subject to strained tendons in the lower leg portions which require frequent treatment, e.g. cooling, in order to keep the animal in top physical condition. While various leg bathing devices such as boots are known for conditioning horse's legs, the apparatus is generally cumbersome, not easily portable, and susceptible to being kicked around by the horse causing damage not only to himself, but to the apparatus as well. Accordingly, it is an object of the present invention to provide a cooling type of hydrotherapeutic device which is simple and durable in construction while being compact, relatively light weight which makes it portable, and efficient in its operation.

It is another object of the present invention to provide an improvement in leg type bathing apparatus for animals which eliminates the conventionally utilized boots.

SUMMARY

Briefly, the subject invention is directed to a recirculating cooling type of bath for the limbs of an animal which is easily portable, consisting of a unitary assembly having a cubical tank located at one end of a fiberglass tub body which includes an enclosed compartment at the other end for housing liquid cooling and circulating apparatus coupled to the tank in a closed circuit as well as means such as an air compressor for coupling compressed air to the bottom of the tank. A vertically aligned recess is formed in one end wall of the tank wherein there is located an evaporator coil assembly coupled to the refrigeration apparatus located in the adjacent compartment. A generally tubular casing is fitted around the evaporator in the recess and having a generally horizontal slot in the upper wall portion which faces into the tank. A liquid input port is located at the bottom of the recess which is coupled to a liquid circulating pump located in the adjacent enclosure whereupon liquid is forced up over the evaporating coil assembly through the tubular casing and out of the slot into the tank. A liquid return port is located in the end wall of the tank adjacent the recess which is coupled back to the circulating pump. Additionally, a filter screen is located in front of the return port for preventing any unnecessary fouling of the circulating pump by debris or other objects being washed into the liquid from the animal's limbs when placed into the tank.

DESCRIPTION OF THE DRAWINGS

FIG. 3 is a transverse cross section of the invention as shown in FIG. 2 taken along the lines 3—3 thereof;

FIG. 4 is a perspective view of a tubular casing surrounding the evaporator unit illustrated in the cut away portion of FIG. 3;

FIG. 5 is a perspective view of the evaporator coil assembly utilized by the subject invention;

FIG. 6 is a perspective view of the filter screen shown in FIG. 3; and

FIG. 7 is a diagram illustrative of the cooling and circulating system of the subject invention shown in combination with fragmentary views of the liquid cooling and circulating means.

DESCRIPTION OF THE PREFERRED EMBODIMENT

Figure 1:
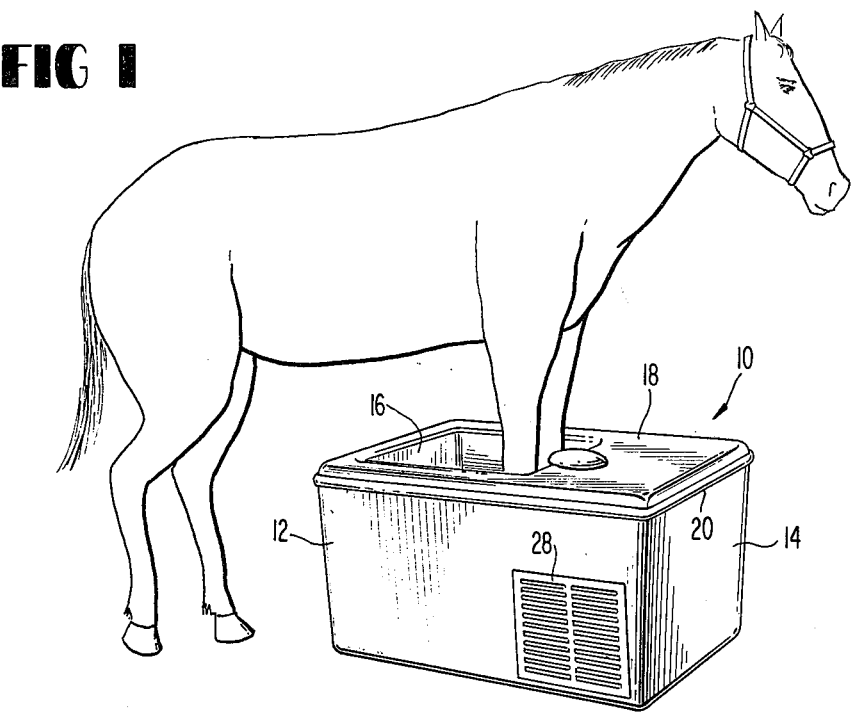
FIG. 1 is a perspective view of the preferred embodiment of the subject invention accommodating the two front legs of a horse.
Figure 2:
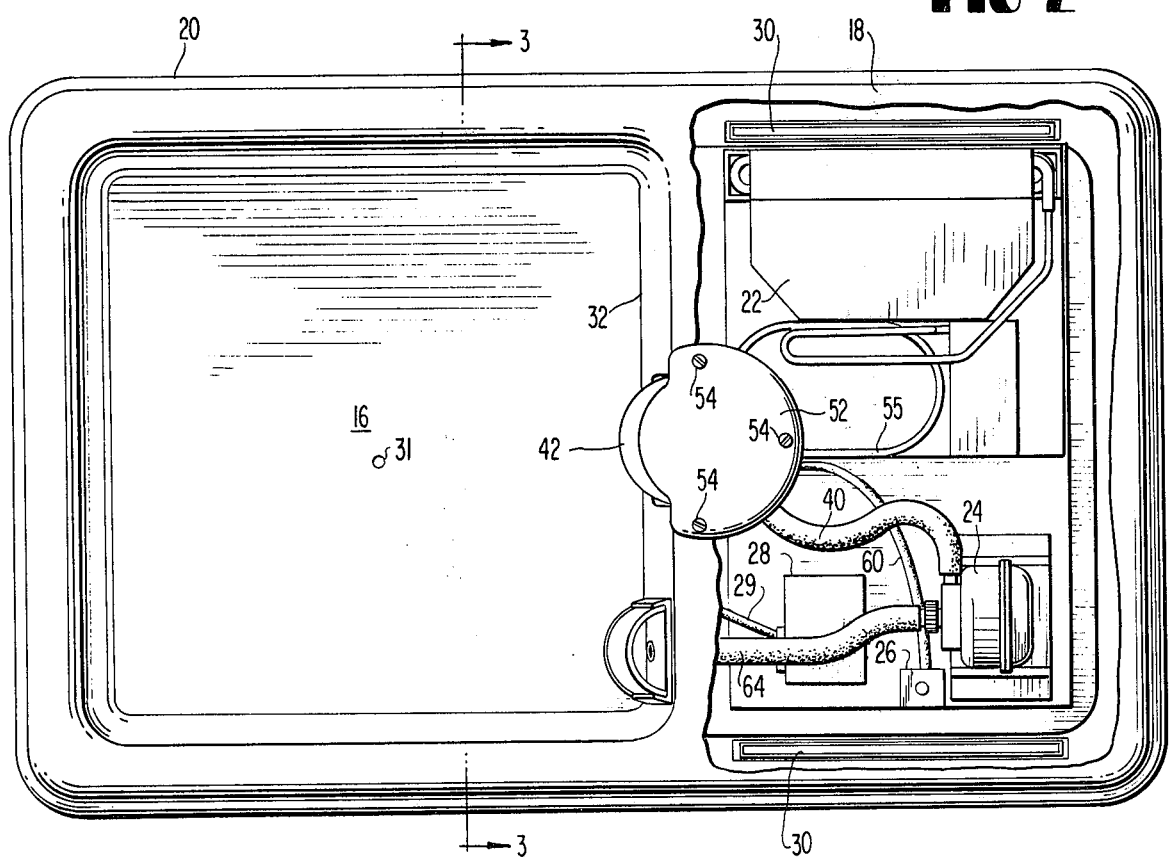
FIG. 2 is a top plan view partially cut away to illustrate the physical layout of the refrigeration unit and circulating pump utilized in connection with the subject invention.

Referring now to the drawings wherein like numerals refer to like parts throughout, reference numeral 10 shown in FIG. 1 denotes a fiber glass tub body having side and end outer walls 12 and 14 which taper inwardly and downwardly toward the ground. An integral fiberglass tank 16 and top wall 18 is fitted to the upper extremities of the side and end walls 14 and secured by means of a suitable closure means 20 as shown in FIG. 3. The tank 16 takes up approximately one-half of the volume of the tub 10 at one end thereof, while the other end comprises an enclosed compartment for accommodating a refrigeration unit 22, a liquid circulating pump 24, a thermostat control unit 26, and an air compressor 28, together with their respective accessories. This is illustrated in FIG. 2. In order to provide air flow through the enclosed compartment as well as conducting heat away from the refrigeration unit 22, a pair of grills 28 and air filters 30 are located in the lower rear portions of the side walls 12 (FIGS. 1 and 3). The relative position of the air filters 30 with respect to the enclosed refrigeration and circulating apparatus is further shown in FIG. 2. The tank 16 is dimensioned (typically 24 × 24 × 24 inches) so as to easily accommodate both the front or rear legs of a large animal such as a race horse, and having a depth so that the lower portion of a horse's legs can be submerged substantially up to its knees for providing a therapeutic refrigerated bath for inflammed tendons and the like. The tank is thus sufficiently large, holding, for example 35 to 40 gallons of water so that the horse is easily able to move about to a limited extent while not being able to harm itself or damage or turn the apparatus over and thus abort the intended therapeutic treatment.

Turning now to the other important features of the subject invention, the rear inner wall 32 of the tank 16 (FIG. 2) includes a vertically aligned recess 34 (FIG.7) which has a liquid input assembly 36 mounted in the lower wall portion 38. The assembly 36 is coupled back to the output of the circulating pump 24 by means of a hose 40. Mounted in the recess 34 is a plastic tubular casing 42 comprising an evaporator shield within which is located an evaporator unit 44 which includes an evaporator coil 46. An input conduit 48 runs through the central axis of the coil 46 while three pieces of copper tubing 50 are secured along the outside of the evaporator coil in order to provide a substantially snug fit of the assembly within the tubular casing 42. The evaporator unit 44 moreover is adapted to be held in place by means of a cap member 52 fitted over the end of the casing 42 and is secured to the fiber-glass top 18 by means of a plurality of screws 54.

Referring to FIG. 7, the refrigeration unit 22 which includes a compressor and condensor, not shown, feeds a compressed gaseous refrigerant to the input conduit 48 by means of tubing 55 where it is then allowed to expand in the evaporator coil 46 and return to the refrigeration unit 22 via tubing 56.

A circulating liquid such as water but, when desirable, may also include epsom salt or other medication is fed from the pump 24 to the bottom of the evaporator unit 44 where it is forced up through the casing 42 around the evaporator coils 46 where it is then cooled for example to 36°-38° F. and forced out of the slot 43 into the tank 16 providing a slightly turbulent action of the liquid around the animal's leg(s). The pump is adapted to move up to 490 gallons per hour. Further agitation of the liquid in the tank 16 is provided by compressed air fed into the bottom wall 33 of the tank from the air compressor 28 by means of an air hose 29 coupled to an outlet 31 as shown in FIG. 7. The air compressor 28 is adapted to be turned on and off by a switch, not shown, at will to suit the needs of the user. The temperature of the liquid is controlled by means of a temperature sensing element 58 shown in FIG. 7, which is coupled back to the thermostatic control unit 26 by means of the tubing 60. The thermostat 26, moreover, is coupled to the refrigeration unit 22 and is adapted to provide a variable temperature control between the range of 0° and 55° F.

In order to provide a closed circulation system, the back wall 32 of the tank includes a return port assembly 62 (FIG. 7) which is positioned adjacent the input port assembly 36 whereupon the refrigerated bath liquid is returned to the pump 24 through the hose connection 64. Inasmuch as the level of circulating liquid can be maintained at any desirable level within the tank 16, an elongated semicircular tubular screen 66 is mounted on the back wall 32 of the tank by means of a metal bracket 68 in substantially vertical parallel relationship with the evaporator shield 42 as shown in FIG. 3. The screen 66 is adapted to prevent any debris getting into the tank from being circulated through the pumping system which would otherwise clog it and necessitate undue overhaul and repair.

Thus what has been shown and described is a rugged, compact, unitized piece of equipment which is easily portable and particularly adapted for the hydrotherapeutic treatment of the legs of race horses; however, when desirable, other limbs of animals, including those of humans, e.g. arms and legs, can be treated depending upon the particular need of the user. It is to be understood, therefore, that the term animal is meant to be read in its broadest context. Accordingly, the foregoing description is made by way of illustration only, and is not meant to be interpreted in a limiting sense, since it will be appreciated that the invention is susceptible to modification, variation and change without departing from the spirit and scope of the invention as set forth in the following claims.

I claim as my invention:

1. Hydrotherapeutic apparatus for treating the limbs such as the legs of an animal comprising in combination:
   a unitary and easily transportable tub body including a tank for receiving at least one limb of said animal and a compartment for accommodating circulating and refrigeration apparatus;
   said tank being of a selected size and shape to permit easy ingress and egress of said limb as well as allowing certain freedom of movement of said animal within said tank without injury to itself while preventing any overturning of said tank or other damage to said apparatus;
   said tank further having a wall including a liquid input port therein for supplying a circulating liquid;
   a liquid refrigerant evaporator unit and an outer casing member within which said evaporator unit is located mounted on said wall, said outer casing member having an end defining an opening adjacent said input port for receiving said circulating liquid supplied thereto and an opening in said casing member adjacent to the other end thereof for feeding circulating liquid passing said evaporator unit into said tank;
   refrigeration apparatus including condenser and compressor means coupled to said evaporator unit for cooling said circulating liquid as it passes through said outer casing member from said input port to said opening in said casing;
   a return port selectively located in said tank; and
   liquid circulating apparatus coupled between said input port and said return port for providing a closed circuit liquid circulation system to and from said tank.

2. The apparatus as defined by claim 1 wherein the refrigeration apparatus comprises thermostatically controlled refrigeration apparatus.

3. The apparatus as defined by claim 1 wherein said tank portion is of a generally cubical shape and having a depth of a selected dimension adapted to provide a cooling bath for the lower leg portion of said animal, said lower leg portion including the tendons between the hoof and knee joint.

4. The apparatus as defined by claim 1 wherein said wall includes a recessed wall portion wherein said evaporator unit and said outer casing member is mounted.

5. The apparatus as defined by claim 4 wherein said recessed wall portion is raised above the bottom of said tank and having a generally vertical alignment.

6. The apparatus as defined by claim 5 wherein said outer casing member comprises a substantially rigid cylindrical member for providing protection of said evaporator unit from the limbs of said horse.

7. The apparatus as defined by claim 6 wherein said opening in said casing member comprises a slot formed in said member facing said tank portion.

8. The apparatus as defined by claim 7 wherein said outer casing member protrudes a predetermined distance into said tank and wherein said lot comprises an elongated slot disposed substantially horizontally between the amount of the casing wall protrusion into said tank.

9. The apparatus as defined by claim 4 wherein said return port is located in said tank wall including said recessed wall portion.

10. The apparatus as defined by claim 9 wherein said return port is raised above the bottom of said tank adjacent the location of said input port.

11. The apparatus as defined by claim 10 and additionally including a filter screen member positioned in front of said outlet port.

12. The apparatus as defined by claim 11 wherein said filter screen member comprises an elongated member positioned adjacent said outer casing member and being oriented substantially parallel thereto.

13. The apparatus as defined by claim 4 and additionally including a cover member fitted over the outer casing member at the end opposite from said input port, said cover member being attached to said tub body for securing the outer casing member and evaporator unit against movement within said recessed wall portion.

14. The apparatus as defined by claim 1 and additionally including means coupled to said tank, supplying a gas under pressure to said tank for agitating said circulating liquid by the flow of said gas therethrough.

15. The apparatus as defined by claim 14 wherein said means comprises an air compressor.

* * * * *